United States Patent [19]

Glamkowski et al.

[11] Patent Number: 4,472,414
[45] Date of Patent: Sep. 18, 1984

[54] SPIRO[INDOLO[1,7-ab][1,5]BENZODIAZE-PINE-2,4'-PIPERIDINES]

[75] Inventors: Edward J. Glamkowski, Warren, N.J.; James M. Fortunato, Willow Grove, Pa.; Richard C. Allen, Flemington, N.J.

[73] Assignee: Hoechst-Roussel Pharmaceuticals Incorporated, Somerville, N.J.

[21] Appl. No.: 495,907

[22] Filed: May 18, 1983

[51] Int. Cl.³ .................... A61K 31/55; C07D 487/20
[52] U.S. Cl. ....................................... 424/267; 546/17
[58] Field of Search ........................... 546/17; 424/267

[56] References Cited

U.S. PATENT DOCUMENTS

| | | | |
|---|---|---|---|
| 4,186,199 | 1/1980 | Glamowski et al. | 424/232 |
| 4,192,874 | 3/1980 | Glamowski et al. | 424/248.54 |
| 4,209,625 | 6/1980 | Ong et al. | 546/17 |

OTHER PUBLICATIONS

"Introduction to Organic Chemistry", by Streitweiesr and Heathcock, 2nd Edition, (Macmillan), (1981), p. 253.
"Advanced Organic Chemistry", by Royals, (Prentice-Hall), (1954), pp. 666–667.
Glamowski et al., "J. Het. Chem.", vol. 19, pp. 865–869, (1979).
Glamowski et al., "J. Med. Chem.", vol. 23, No. 12, pp. 1380–1386.

*Primary Examiner*—Robert T. Bond
*Attorney, Agent, or Firm*—Tatsuya Ikeda

[57] ABSTRACT

There are described spiro[indolo[1,7-ab][1,5]benzodiazepine-2,4'-piperidines]of the formula

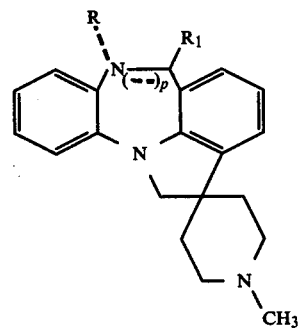

wherein p is 1 or 0, $R_1$ is hydrogen or methyl and R is hydrogen or $-CO(CH_2)_nNR_2R_3$, $R_2$ and $R_3$ being each hydrogen or methyl but at least one of the two being methyl, and n being 1 or 2, which are useful as analgesic agents; intermediate compounds therefor; and methods for synthesizing the foregoing compounds.

19 Claims, No Drawings

SPIRO[INDOLO[1,7-ab][1,5]BENZODIAZEPINE-2,4'-PIPERIDINES]

There are described spiro[indolo[1,7-ab][1,5]benzodiazepine-2,4'-piperidines] of the formula

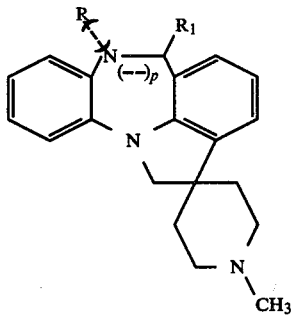
(I)

wherein p is 1 or 0, $R_1$ is hydrogen or methyl and R is hydrogen or $—CO(CH_2)_nNR_2R_3$, $R_2$ and $R_3$ being each hydrogen or methyl but at least one of the two being methyl, and n being 1 or 2, which are useful as analgetic agents; intermediate compounds therefor; and methods for synthesizing the foregoing compounds.

Throughout the specification and appended claims, the optional additional bond (----)$_p$ in the above Formula I is a full bond when p is 1 but is nonexistent when p is 0, and the other optional bond (----) between the nitrogen atom and group R in Formula I is nonexistent when p is 1 and is a full bond when p is 0.

Thus, the above depicted Formula I may be

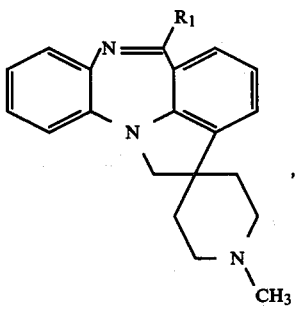
(II)

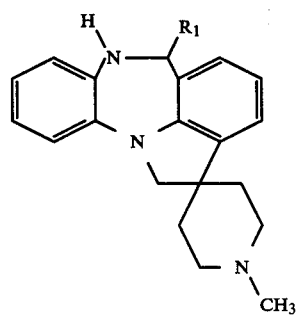
(III)

or

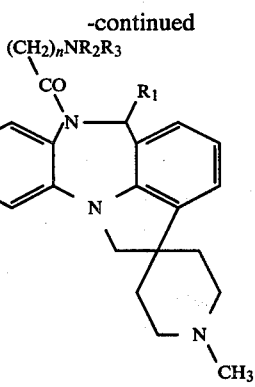
(IV)

The novel intermediate compounds of this invention useful for synthesizing compounds of Formula I are

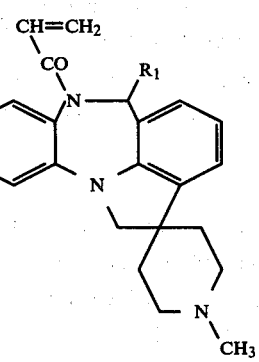
(V)

and

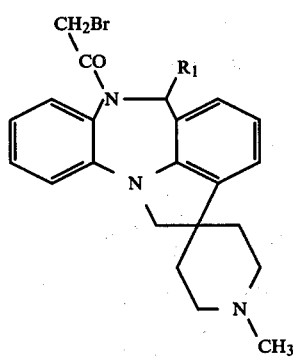
(VI)

As can be seen from the Formulas V and VI, these intermediate compounds correspond to the situation where p is 0 and R is $—COCH=CH_2$ or $—COCH_2Br$ in Formula I.

To the best of our knowledge the compounds of the present invention have not been described or suggested.

Throughout the specification and the appended claims, a given chemical formula or name shall encompass all stereo isomers thereof if such isomers exist.

The compounds of the present invention are prepared by following one or more of the steps described below. The groups $R_1$, $R_2$ and $R_3$ have the same significance as defined above throughout the specification and the claims.

STEP A

The compound of Formula II is prepared by the cyclodehydration of a compound of the formula

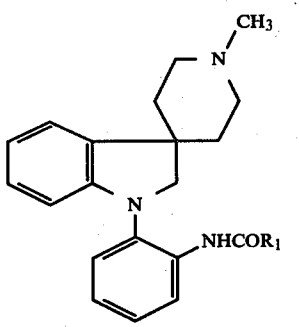

(VII)

in the presence of a suitable reagent such as POCl₃. Typically, POCl₃ is added slowly to the reactant and then the reaction mixture is heated at an elevated temperature such as 100°–120° C. for one to several hours. The starting compounds of Formula VII (R₁ is hydrogen or methyl) are described in Ong et al. U.S. Pat. No. 4,209,625.

STEP B

The compound of Formula III is prepared by reducing the compound of Formula II by use of a suitable reducing agent such as NaBH₄ in a suitable solvent such as ethanol. Typically, NaBH₄ is added to the reactant in small portions at ice temperature and the reaction continued overnight at room temperature.

STEP C

A compound of the formula

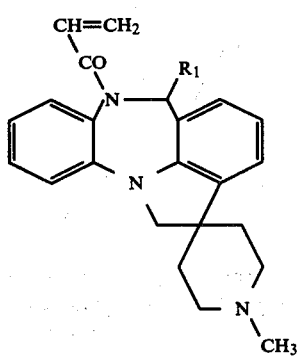

(V)

is prepared by reacting the compound of Formula III with an acryloyl halide (halide being chloride, bromide or fluoride, preferably chloride) in a suitable solvent such as methylene chloride in the presence of an acid scavenger such as potassium carbonate. Typically, the reaction is conducted using acryloyl chloride between ice temperature and room temperature for a period of 1–2 hours.

STEP D

A compound of the formula

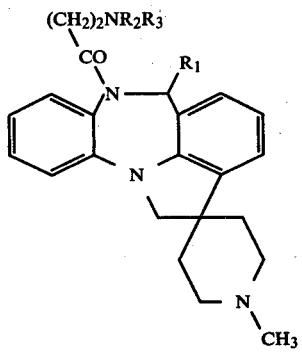

(IVa)

is prepared by reacting the compound of Formula V with an amine of the formula HNR₂R₃ in a suitable solvent such as absolute ethanol. Typically, the amine is slowly bubbled into an ethanolic solution of the reactant and the reaction is continued at room temperature for about one hour.

STEP E

A compound of the formula

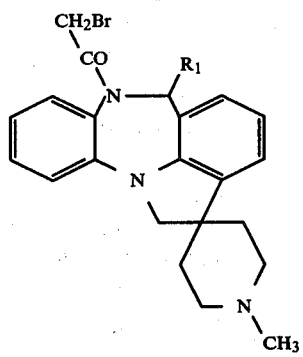

(VI)

can be prepared by reacting the compound of Formula III with bromoacetyl bromide in a suitable solvent such as methylene chloride in the presence of an acid scavenger such as potassium carbonate.

STEP F

A compound of the formula

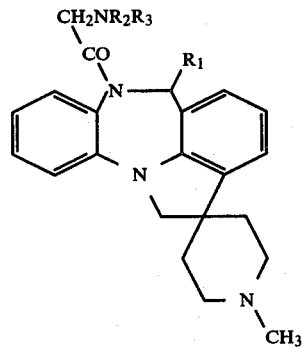

(IVb)

can be prepared by reacting the compound of the Formula VI with an amine of the formula HNR₂R₃ in a suitable solvent such as absolute ethanol.

All other starting materials shown above are either known compounds or easily prepared by routine methods known to the art from readily available materials.

Compounds of Formula I of the present invention, namely, compounds of Formulas II, III and IV are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 1 shows a result of the test of the analgesic activities of some of the compounds of this invention.

TABLE 1

ANALGESIC ACTIVITY
(Phenylquinone Writhing)

| Compound | Inhibition of Writing $ED_{50}$ (mg/kg, sc) |
|---|---|
| 1,2-dihydro-1'-methyl-spiro[indolo[1,7-ab]-[1,5]benzodiazepine-2,4'-piperidine]dihydrochloride | 12.1 |
| 1,2-dihydro-1',6-dimethyl-spiro[indolo-[1,7-ab][1,5]benzodiazepine-2,4'piperidine]dihydrochloride | 4.7 |
| 1',6-dimethyl-1,2,6,7-tetrahydro-spiro[indolo-[1,7-ab][1,5]benzodiazepine-2,4'-piperidine]dihydrochloride | 9.7 |
| 7-(N,N—dimethyl-3-aminopropionyl)-1',6-dimethyl-1,2,6,7-tetrahydro-spiro[indolo[1,7-ab][1,5]-benzodiazepine-2,4'piperidine]dihydrobromide | 28.4 |

The compounds of the invention compare favorably with the well known analgesic compound ibuprofen, which, in a similar test exhibited an analgesic $ED_{50}=10.4$ mg/kg, orally.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free acid final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
1,2-dihydro-1',6-dimethyl-spiro[indolo[1,7-ab][1,5]benzodiazepine-2,4'-piperidine];
1,2-dihydro-1'-methyl-spiro[indolo[1,7-ab]]1,5]benzodiazepine-2,4'-piperidine];
1',6-dimethyl-1,2,6,7-tetrahydro-spiro[indolo[1,7-ab][1,5]benzodiazepine-2,4'-piperidine];
7-acryloyl-1',6-dimethyl-1,2,6,7-tetrahydro-spiro[indolo[1,7-ab][1,5]-benzodiazepine-2,4'-piperidine]; and
7-(N,N-dimethyl-3-aminopropionyl)-1',6-dimethyl-1,2,6,7-tetrahydro-spiro[indolo[1,7-ab][1,5]benzodiazepine-2,4'-piperidine]

The following examples are given for illustrative purposes and are not to be considered as limiting the invention disclosed herein. All temperatures are given in degrees Celcius.

EXAMPLE I 1,2-Dihydro-1'-methyl-spiro[indolo[1,7-ab][1,5]benzodiazepine-2,4'-piperidine]dihydrochloride In a 1 liter round bottom flask, 10.0 g (31.2 mmole) of 1-(2-formamidophenyl)-1'-methyl-spiro[indoline-3,4'-piperidine] was placed and 75 ml of $POCl_3$ was added thereto. An immediate pink to brown-green color change was observed along with an exotherm. The reaction mixture was cooled in an ice bath and any large lumps of HCl salt were broken up with a spatula. After 5 minutes at 0°, the dark slurry was permitted to warm to room temperature and then heated at 100° for 1 hour. POCl₃ was then distilled at water aspirator pressure and the residue was boiled up with 200 ml of absolute EtOH. The solid was filtered, washed with EtOH and then with dry ether, and air dried to afford 7.99 g of a crude di-hydrochloride salt.

A solution of the salt in 300 ml water was made basic using concentrated NH₄OH. The free base was extracted with CH₂Cl₂ (300 ml), washed with water (300 ml) and brine (400 ml), dried (Na₂SO₄) and concentrated to give 4.59 g of product. A filtered solution of this free base in 50 ml dry ether and 20 ml MeOH was added to 150 ml of rapidly stirred ice cold ethereal HCl. The salt was filtered, washed with dry ether and dried under vacuum (77°/0.25 mmHg) to afford 4.95 g (42.3% overall) of analytically pure material, m.p. greater than 310°.

ANALYSIS: Calculated for $C_{20}H_{21}N_3.2HCl$: 63.83% C; 6.16% H; 11.16% N; 18.84% Cl. Found: 63.93% C; 6.12% H; 11.15% N; 18.61% Cl.

EXAMPLE II 1,2-Dihydro-1',6-dimethyl-spiro[indolo[1,7-ab][1,5]benzodiazepine-2,4'-piperidine]dihydrochloride 34.2 g (0.10 mole) of 1-(2-acetylaminophenyl)-1-methylspiro-[indoline-3,4'-piperidine] and 200 ml of POCl₃ placed in a 1 liter round bottom flask under N₂ were slowly heated over 2 hours to 109°. Within 5 minutes after the addition of the POCl₃, the reaction mixture became a solid, and at 70° the product thinned to a stirrable slurry. After 5 hours at 109°–116° the product was permitted to cool to room temperature and stand overnight.

The POCl₃ was distilled at water aspirator pressure and the resulting residue was triturated with hexane, filtered, washed with additional hexane and dried under a high vacuum at 80° to afford 49.89 g of a solid.

The crude salt was dissolved in a mixture of EtOH (800 ml) and 10% aqueous NaOH (800 ml) and the resulting solution was filtered and concentrated. The residue was dissolved in CH₂Cl₂, washed with brine, dried and concentrated on a rotary evaporator to afford 46.7 g of a crude free base. Conversion of the base back to the HCl salt (ethanolic HCl) afforded 20.78 g (52.5%) of a solid, m.p. 295° C., dec.

Recrystallization from MeOH-ether yielded 18.81 g (47.3% overall) of pure di-HCl salt, m.p. 303° C., dec.

ANALYSIS: Calculated for $C_{21}H_{23}N_3.2HCl$: 64.62% C; 6.46% H; 10.76% N; 18.16% C. Found: 64.83% C; 6.57% H; 10.90% N; 18.00% Cl.

EXAMPLE III

1',6-Dimethyl-1,2,6,7-tetrahydro-spiro[indolo[1,7-ab][1,5]benzodiazepine-2,4'-piperidine]dihydrochloride 30 g of NaBH₄ was added portionwise over 2⅔ hours to an ice-cold, rapidly stirred solution of 60.1 g (190 mmole) of 1,2-dihydro-1',6-dimethyl-spiro[indolo[1,7-ab][1,5]benzodiazepine-2,4'-piperidine] in 450 ml absolute EtOH. After standing overnight at room temperature, the mixture was cooled to 0°, treated dropwise with 625 ml of water, and partially concentrated on a rotary evaporator. The resulting solid was filtered and dissolved in CHCl₃. This organic portion was then washed with 10% aqueous NaOH (600 ml), water (600 ml) and brine (600 ml), dried over MgSO₄ and concentrated to give 78.09 g of a crude material.

A 14.21 g portion of the crude material was chromatographed (750 g silica gel; ether-methylene chloride-methanol) to afford 5.31 g of the pure amine. Conversion to the di-HCl salt (Et₂O—CH₂Cl₂/ethereal HCl) afforded 6.44 g of pure product salt, m.p. 293°, dec. in 47% overall yield.

ANALYSIS: Calculated for $C_{21}H_{25}N_3.2HCl$: 64.28% C; 6.94% H; 10.71% N. Found: 64.50% C; 7.17% H; 10.50% N.

EXAMPLE IV

7-Acryloyl-1',6-dimethyl-1,2,6,7-tetrahydro-spiro[indolo[1,7-ab][1,5]-benzodiazepine-2,4'-piperidine]hydrochloride A solution of 1.7 ml (21.21 mmole) of freshly distilled acryloyl chloride in 1.8 ml CH₂Cl₂ was added dropwise over 5 minutes to an ice-cold rapidly stirred slurry of 6.16 g (19.28 mmole) of 1',6-dimethyl-1,2,6,7-tetrahydro-spiro[indolo[1,7-ab][1,5]benzodiazepine-2,4'-piperidine] and 2.93 g (21.21 mmole) of K₂CO₃ in 40 ml CH₂Cl₂. After 30 minutes an additional 10 drops of acryloyl chloride were added and the mixture was stirred for another 45 minutes before work-up. The product was washed twice with 5% NaOH (150 ml), dried over Na₂SO₄, filtered and concentrated to give 6.97 g (96.8%) of a crude amide.

Chromatography on silica gel (ether-methylene chloride-methanol) afforded 5.01 g (69.6% overall) of a pure amide. A portion of the free base was converted to the hydrochloride salt (ether/ethereal HCl), m.p. 265°, dec.

ANALYSIS: Calculated for $C_{24}H_{27}N_3O.HCl$: 70.32% C; 6.88% H; 10.25% N; 8.65% Cl. Found: 69.58% C; 6.93% H; 10.09% N; 8.67% Cl.

EXAMPLE V 7-(N,N-dimethyl-3-aminopropionyl)-1',6-dimethyl-1,2,6,7-tetrahydro-spiro[indolo[1,7-ab][1,5]benzodiazepine-2,4'-piperidine]dihydrobromide Dimethylamine gas was slowly bubbled into a rapidly stirred solution of 3.0 g (8.03 mmole) of 7-acryloyl-1',6-dimethyl-1,2,6,7-tetrahydro-spiro[indolo[1,7-ab][1,5]benzodiazepine-2,4'-piperidine] in 80 ml of absolute EtOH at room temperature. After 1 hour, TLC analysis showed no starting material. The ethanolic solution was concentrated on a rotary evaporator and the residue was dissolved in methylene chloride (100 ml), washed with water (125 ml) and brine (125 ml), dried over Na₂SO₄, and concentrated to give 2.92 g (86.9%) of the free base.

Conversion to the di-HBr salt (ether/ethereal HBr) and multiple precipitations from ethanol-ether afforded 1.0 g (21.4%) of pure dihydrobromide salt, m.p. 211°, dec.

ANALYSIS: Calculated for $C_{26}H_{34}N_4O.2HBr$: 53.80% C; 6.25% H; 9.65% N. Found: 54.15% C; 6.33% H; 9.77% N.

We claim:

1. A compound having the formula

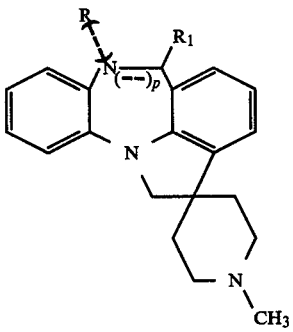

wherein p is 1 or 0, $R_1$ is hydrogen or methyl and R is hydrogen, —$CO(CH_2)_nNR_2R_3$, —$COCH=CH_2$ or —$COCH_2Br$, $R_2$ and $R_3$ being each hydrogen or methyl but at least one of the two being methyl, and n being 1 or 2, or a pharmaceutically acceptable acid addition salt thereof.

2. The compound as defined in claim 1 wherein p is 1, which is

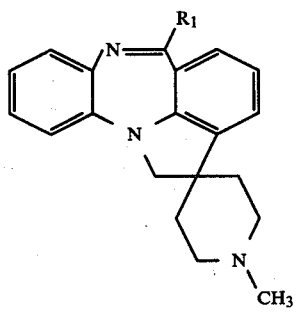

or a pharmaceutically acceptable acid addition salt thereof.

3. The compound as defined in claim 2 wherein $R_1$ is hydrogen, which is 1,2-dihydro-1'-methyl-spiro[indolo[1,7-ab][1,5]benzodiazepine-2,4'-piperidine], or a pharmaceutically acceptable acid addition salt thereof.

4. The compound as defined in claim 2 wherein $R_1$ is methyl, which is 1,2-dihydro-1',6-dimethyl-spiro[indolo[1,7-ab][1,5]benzodiazepine-2,4'-piperidine], or a pharmaceutically acceptable acid addition salt thereof.

5. The compound as defined in claim 1 wherein p is 0 and R is hydrogen, which is the compound of the structure:

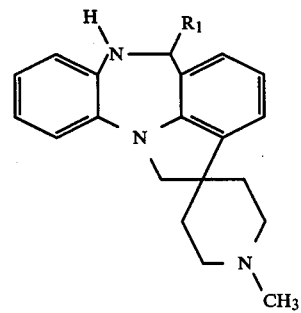

or a pharmaceutically acceptable acid addition salt thereof.

6. The compound as defined in claim 5 wherein $R_1$ is hydrogen, which is 1'-methyl-1,2,6,7-tetrahydro-spiro[indolo[1,7-ab][1,5]-benzodiazepine-2,4'-piperidine], or a pharmaceutically acceptable acid addition salt thereof.

7. The compound as defined in claim 5 wherein $R_1$ is methyl, which is 1,6'-dimethyl-1,2,6,7-tetrahydro-spiro[indolo[1,7-ab][1,5]-benzodiazepine-2,4'-piperidine], or a pharmaceutically acceptable acid addition salt thereof.

8. The compound as defined in claim 1 wherein p is 0 and R is —$CO(CH_2)_nNR_2R_3$, which is the compound of the formula

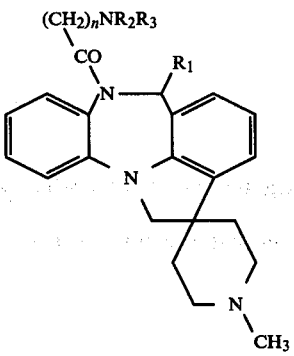

or a pharmaceutically acceptable acid addition salt thereof.

9. The compound as defined in claim 8 wherein n is 1.

10. The compound as defined in claim 8 wherein n is 2.

11. The compound as defined in claim 10 wherein $R_1$ is methyl.

12. The compound as defined in claim 11 wherein $R_2$ and $R_3$ are methyl, which is 7-(N,N-dimethyl-3-aminopropionyl)-1',6-dimethyl-1,2,6,7-tetrahydro-spiro[indolo[1,7-ab][1,5]benzodiazepine-2,4'-piperidine], or a pharmaceutically acceptable acid addition salt thereof.

13. The compound as defined in claim 1 wherein p is 0 and R is —$COCH=CH_2$ which is the compound of the formula

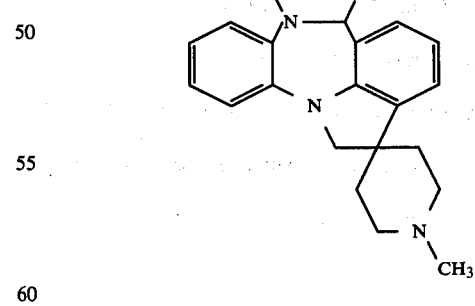

14. The compound as defined in claim 13 wherein $R_1$ is methyl, which is 7-acryloyl-1',6-dimethyl-1,2,6,7-tetrahydro-spiro[indolo[1,7-ab][1,5]benzodiazepine-2,4'-piperidine].

15. The compound as defined in claim 1, wherein p is 0 and R is —$COCH_2Br$ which is the compound of the formula

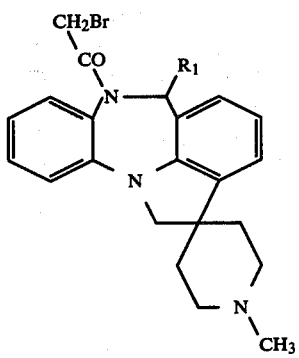

16. An analgesic composition which comprises an effective pain alleviating amount of a compound having the formula

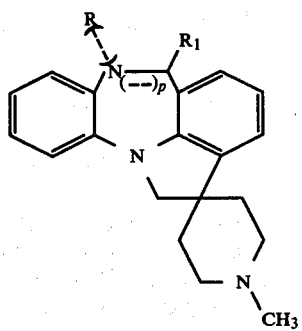

wherein p is 1 or 0, $R_1$ is hydrogen or methyl and R is hydrogen or —CO(CH$_2$)$_n$NR$_2$R$_3$, R$_2$ and R$_3$ being each hydrogen or methyl but at least one of the two being methyl, and n being 1 or 2, or a pharmaceutically acceptable acid addition salt thereof.

17. The analgesic composition as defined in claim 16 which comprises an effective pain alleviating amount of a compound of the formula

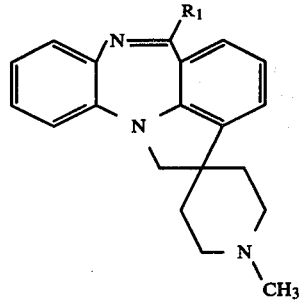

or a pharmaceutically acceptable acid addition salt thereof.

18. The analgesic composition as defined in claim 16 which comprises an effective pain alleviating amount of a compound of the formula

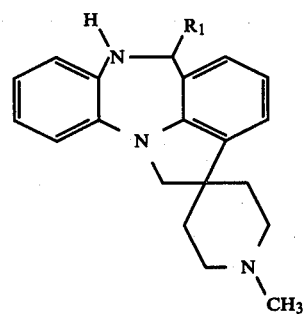

or a pharmaceutically acceptable acid addition salt thereof.

19. The analgesic composition as defined in claim 16 which comprises an effective pain alleviating amount of a compound of the formula

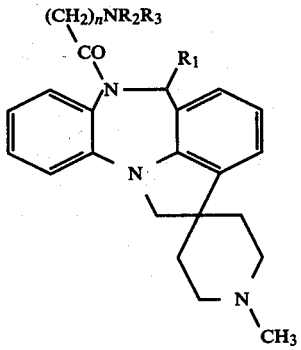

or a pharmaceutically acceptable acid addition salt thereof.

* * * * *